United States Patent
Fix et al.

(10) Patent No.: US 8,961,760 B2
(45) Date of Patent: Feb. 24, 2015

(54) MICROMECHANICAL SOLID-ELECTROLYTE SENSOR DEVICE AND CORRESPONDING PRODUCTION METHOD

(71) Applicant: Robert Bosch GmbH, Stuttgart (DE)

(72) Inventors: Richard Fix, Gerlingen (DE); Andreas Krauss, Tuebingen (DE)

(73) Assignee: Robert Bosch GmbH, Stuttgart, DE (US)

( * ) Notice: Subject to any disclaimer, the term of this patent is extended or adjusted under 35 U.S.C. 154(b) by 19 days.

(21) Appl. No.: 13/746,345

(22) Filed: Jan. 22, 2013

(65) Prior Publication Data
US 2013/0192989 A1     Aug. 1, 2013

(30) Foreign Application Priority Data
Jan. 31, 2012   (DE) .......................... 10 2012 201 304

(51) Int. Cl.
*G01N 27/407*  (2006.01)
*G01N 27/414*  (2006.01)

(52) U.S. Cl.
CPC ........ G01N 27/4071 (2013.01); G01N 27/4141 (2013.01)
USPC ............ 204/424; 73/23.31; 73/23.32; 216/17

(58) Field of Classification Search
USPC ...................... 204/421–429; 73/23.31; 216/17
See application file for complete search history.

(56) References Cited

U.S. PATENT DOCUMENTS

| | | | | |
|---|---|---|---|---|
| 6,905,615 | B2* | 6/2005 | Fischer et al. ..................... | 216/2 |
| 7,160,750 | B2* | 1/2007 | Benzel et al. ................... | 438/48 |
| 7,655,333 | B2* | 2/2010 | Huang et al. ................... | 429/495 |
| 2007/0138581 | A1* | 6/2007 | Baer et al. ..................... | 257/414 |
| 2009/0129440 | A1* | 5/2009 | Opitz et al. ................... | 374/178 |
| 2009/0181278 | A1* | 7/2009 | Son et al. ........................ | 429/30 |

FOREIGN PATENT DOCUMENTS

DE      199 41 051 A1    3/2001

* cited by examiner

*Primary Examiner* — Jennifer Dieterle
(74) *Attorney, Agent, or Firm* — Maginot, Moore & Beck LLP

(57) ABSTRACT

A micromechanical solid-electrolyte sensor device includes a micromechanical carrier substrate having a front side and a back side. The micromechanical solid-electrolyte sensor device also includes a first porous electrode and a second porous electrode. The micromechanical solid-electrolyte sensor device also includes a solid-electrolyte embedded between the first porous electrode and the second porous electrode.

11 Claims, 3 Drawing Sheets

MICROMECHANICAL SOLID-ELECTROLYTE SENSOR DEVICE AND CORRESPONDING PRODUCTION METHOD

This application claims priority under 35 U.S.C. §119 to patent application no. DE 10 2012 201 304.0, filed on Jan. 31, 2012 in Germany, the disclosure of which is incorporated herein by reference in its entirety.

BACKGROUND

The disclosure relates to a micromechanical solid-electrolyte sensor device and to a corresponding production method.

Solid-electrolyte gas sensors are known in the prior art, for example as an oxygen sensor in the form of a lambda probe. A lambda probe formed as a Nernst probe measures the voltage of a solid electrolyte, zirconium dioxide being used as a membrane. The property of zirconium dioxide that it can electrolytically transport oxygen ions at elevated temperature (typically 650° C. in the case of ceramic probes), so that a measurable voltage is formed, is utilized in this case.

DE 199 41 051 A1 discloses a gas sensor which is formed as a broadband lambda probe, which comprises a ceramic solid-electrolyte base and a plurality of electrodes that are applied in chambers and on the outer side of the solid electrolyte.

As the technology for such known solid-electrolyte sensor devices, the ceramic thick-film technology is used, which only permits relatively large minimum dimensions both for the structural widths (typically more than 30 µm) and for the layer thicknesses (typically more than 10 µm). By combining a plurality of cells, besides oxygen sensors it is also possible to produce other types of gas sensors, for example for nitrogen oxides, but these are expensive and require complicated evaluation electronics.

SUMMARY

The disclosure relates to a micromechanical solid-electrolyte sensor device as described below and to a corresponding production method as described below.

The description below relates to preferred refinements.

The concept on which the present disclosure is based is the use of micromechanical technologies for solid-electrolyte based gas sensors. The disclosure therefore permits further miniaturization of such sensors, reduces the costs and increases the reliability by integration possibilities for further sensor elements, for example for evaluation and driver circuits.

In particular, the disclosure combines chemical functional materials and functional mechanisms of ceramic thick-film gas sensors, for example a solid electrolyte as oxygen-conductive material, with processes, structures and materials of microsystem technology, for example microstructured membranes for producing said gas sensors. The production of much smaller dimensions in electrode and solid-electrolyte materials allows expedient utilization of material properties and, for example, allows extension of the temperature range.

Advantageous refinements and improvements of the device and method described below are possible by virtue of the measures described below.

It is advantageous for the carrier substrate to comprise an open cavern for establishing a membrane region, and for the second porous electrode to extend through the cavern. This makes it possible to manufacture a sensor structure by backside micromechanics, so that a multiplicity of small and stable membranes formed on a wafer and subsequently contacted simultaneously in a sensor (by electrodes extending on the front side and back side) can be used.

It is furthermore advantageous for the carrier substrate to comprise a porosified region above which the first porous electrode, the second porous electrode and the solid electrolyte, embedded between the first porous electrode and the second porous electrode, are provided. By virtue of this measure, the backside micromechanics are obviated, the carrier substrate remains more stable and there is no membrane susceptible to pressure. By virtue of the porosification, the gas to be detected nonetheless reaches the sensor or, in pump operation, the gas pumped through the electrolyte can flow away.

It is furthermore advantageous for the carrier substrate to comprise a closed cavern, and for the second porous electrode to extend through the closed cavern. This measure allows diffusion-limited operation of the sensor. An electrical connection is established with the porous electrode, and at the same time gas can also flow in, or flow away, in a defined way through the porous layer.

It is furthermore advantageous for the micromechanical carrier substrate to be part of a wafer. By virtue of this measure, parallel production of a plurality of sensors simultaneously on a wafer is possible, and specifically throughout all the working steps (application of solid electrolyte, electrodes, generation of cavities etc.). Electronic circuits may still furthermore be integrated in the wafer, and corresponding processing may preferably already take place beforehand so that the active sensor layers are not compromised.

It is furthermore advantageous for the wafer to consist of Si, SiC or sapphire. An advantage with this measure is that an economical substrate can be produced, which is simple to process and allows simple integration of the electronics. SiC is furthermore very stable at high temperature and permits electronic components in the sensor at temperatures of up to 500° C. or more. Sapphire is nonconductive even without an additional insulating material.

It is furthermore advantageous if an auxiliary membrane is provided on the front side of the carrier substrate before the cavern is formed, the cavern is subsequently etched, the solid electrolyte and the first porous electrode are next provided on the front side, then the auxiliary membrane is removed from the back side, and finally the second porous electrode is applied in such a way that it extends through the cavern. This measure permits simpler and more reliable manufacture. According to the prior art, a membrane is produced as a first step by a backside micromechanical process (for example wet etching of Si with KOH etch). The reject rate is comparatively high in this case (in comparison with the deposition of the sensor layers). When starting with this process step, loss can be minimized since only few processed wafers are destroyed in the event of a defect. Furthermore, with this procedure a layer which is later active in the sensor (for example the solid electrolyte) is not exposed to the etchant or the etching method for the wafer. The membrane material can be selected in such a way that the selectivity of the etching of the membrane in relation to the solid electrolyte is optimal. Since the membrane is also much thinner than the wafer, any possibly necessary overetching of the membrane can turn out to be much shorter than in the case of direct etching of the wafer. In this case, the unremoved auxiliary membrane material remaining outside the membrane region can undertake the insulation of the solid electrolyte from the substrate.

It is furthermore advantageous if the solid electrolyte and the first porous electrode are provided on the front side before the cavern is formed, an auxiliary membrane is subsequently provided on the front side of the carrier substrate, the cavern is then etched, the second porous electrode is next applied in such a way that it extends through the cavern, and the auxiliary membrane on the front side is finally removed. This is a particularly advantageous method for integrating electronics on the wafers for the sensors. The wafers with electronics are fully (pre)processed. Then the sensor layers are applied on these wafers (preferably in an only locally limited way) and an auxiliary membrane, for example consisting of a polymer, is applied on these wafers either in a locally limited way or surface-wide. After the end of the processing of the cavern, the auxiliary membrane consisting of a polymer is removed, for example using a solvent.

BRIEF DESCRIPTION OF THE DRAWINGS

Other features and advantages of the present disclosure will be explained below with the aid of the embodiments with reference to the figures, in which.

DETAILED DESCRIPTION

In the figures, references which are the same refer to identical or functionally equivalent elements.

Figure 1:
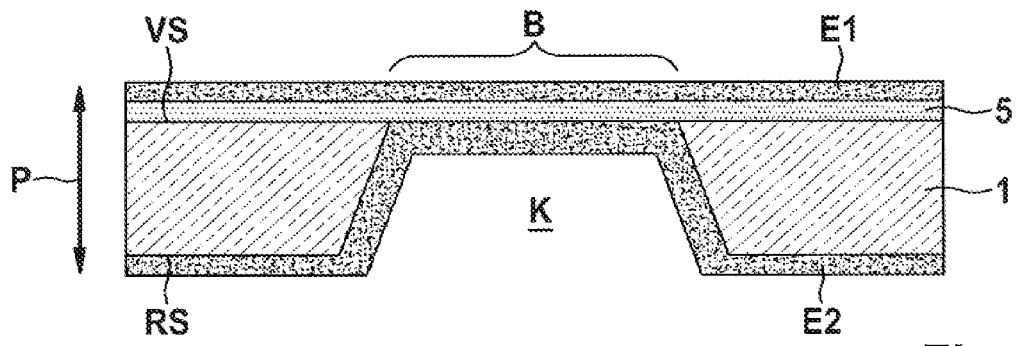
FIG. 1 shows a schematic cross-sectional view to explain a micromechanical solid-electrolyte sensor device according to a first embodiment of the present disclosure.

FIG. 1 is a schematic cross-sectional view to explain a micromechanical solid-electrolyte sensor device according to a first embodiment of the present disclosure.

In FIG. 1, reference 1 denotes a carrier substrate having a front side VS and a back side RS. Provided in the carrier substrate 1, there is a cavern K which extends from the back side RS to the front side VS. A solid-electrolyte membrane 5 is applied over the front side VS of the carrier substrate 1 in such a way that it covers the cavern K and the peripheral region thereof. On the solid-electrolyte membrane 5, a first electrode E1 is applied on the front side and a second electrode E2 is applied on the back side, the electrodes E1, E2 being porous, or gas-permeable. This structure forms a simple Nernst cell. The carrier substrate 1 is in particular part of a wafer of a semiconducting or insulating material, for example Si, SiC or sapphire. By using thin-film methods, or by virtue of methods which are conventional in the semiconductor field, both for the functional materials of the solid-electrolyte membrane 5 and of the electrodes E1, E2 and for the carrier substrate 1, structural widths and layer thicknesses can be reduced significantly.

For example, a layer thickness for the solid-electrolyte membrane 5 of from a few nanometers, for example 10 nm, to several micrometers, for example 10 μm, is possible. For the formation of the membrane region B, a thickness range of from 300 nm to 2 μm is preferred. The lateral dimensions of a single such Nernst cell may vary from 1 μm to several hundreds of μm.

In particular, by using a solid electrolyte for the solid-electrolyte membrane 5 with a small layer thickness, parasitic series resistances can be reduced so that relatively high Nernst currents are also possible. By means of the smaller layer thicknesses, the grain sizes are also limited. For the nanoscale solid-state electrolytes which are thus possible, it is therefore also possible to achieve lower operating temperatures in the range of less than 500° C., or up to at least 800° C., in addition to high gastightness.

As a production method for the solid-electrolyte membrane 5, it is possible to use physical deposition methods, for example sputtering or laser ablation, or chemical deposition methods, in particular chemical vapor deposition and atomic layer deposition. Larger layer thicknesses for the solid electrolyte can also be produced by means of conventional ceramic thick-film technology, for example by screen printing, on micromechanical carrier substrates 1, which provides a hybrid overall system. In this case, the printing, or the deposition of the solid electrolyte, preferably takes place before the formation of the cavern and the application of the backside electrode E2.

Preferably, an individual Nernst cell is configured to be as small as possible, in order to achieve high stability in the membrane region B.

By combining a plurality of individual membranes, a pump cell with large area and great current signal can be achieved. To this end it is merely necessary for the electrode coatings in the individual Nernst cells to be connected, which in the simplest case is done by forming the electrodes E1, E2 so that they extend over a carrier substrate 1 having a multiplicity of caverns K and corresponding membrane regions B.

If the carrier substrate 1 is not gas-permeable, then it should have a layer for insulation from the solid electrolyte, since otherwise a pump process which can destroy the Nernst cell also takes place in the regions without gas permeability. This insulation layer may be either electrical in nature so that no field, by means of which a gas can be pumped, is locally set up in the solid electrolyte. As an alternative, a gastight layer may be used, which prevents gas from reaching regions of the solid-electrolyte layer.

For the production, a solid electrolyte is expediently initially applied on the front side VS on a carrier substrate 1, on the regions intended for the Nernst cell or the Nernst cells, and the front-side electrode E1 is applied thereon. By means of a structuring method, for example wet etching or DRIE (Deep Reactive Ion Edging), the carrier substrate 1 is then removed from the back side RS as far as the front side VS. In the case of a multilayered structure of the carrier substrate 1 (for example in the case of an aforementioned insulation layer on the carrier substrate 1 on the front side VS under the solid-electrolyte membrane 5), the structuring method may comprise a plurality of stages. After the structuring of the carrier substrate 1 from the back side in order to produce the cavern K, or the caverns K, the coating of the backside electrode E2 is carried out from the back side RS.

It should be noted that reference P in FIG. 1 denotes the pumping direction for the gas, in this case oxygen, which is reversible depending on the direction of the applied voltage in the membrane region B.

Figure 2:
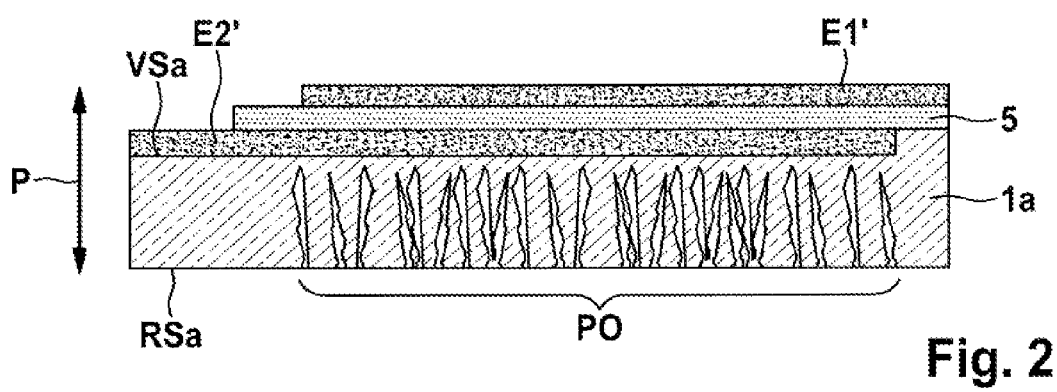
FIG. 2 shows a schematic cross-sectional view to explain a micromechanical solid-electrolyte sensor device according to a second embodiment of the present disclosure.

FIG. 2 is a schematic cross-sectional view to explain a micromechanical solid-electrolyte sensor device according to a second embodiment of the present disclosure.

In the embodiment according to FIG. 2, reference 1a denotes a carrier substrate, which has a front side VSa and a back side RSa. A porous region PO extends from the back side RSa to the front side VSa. In the Nernst cell according to FIG. 2, the carrier substrate 1a is used on the one hand as a carrier for the solid-electrolyte membrane 5 and the electrodes E1', E2', and at the same time as a diffusion barrier for the function of the Nernst cell.

For the production, the backside electrode E2' is deposited on the front side VSa of the carrier substrate 1a, the solid electrolyte for the solid-electrolyte membrane 5 is deposited thereon and the front-side electrode E1' is deposited on top.

Advantageously, at least one of the electrodes E1', E2' is laterally structured. Finally, the carrier substrate is porosified from the back side RSa, specifically at least in a region PO on which the two electrodes E1', E2' are present and in which pumping takes place owing to the solid-electrolyte membrane 5.

Figure 3:
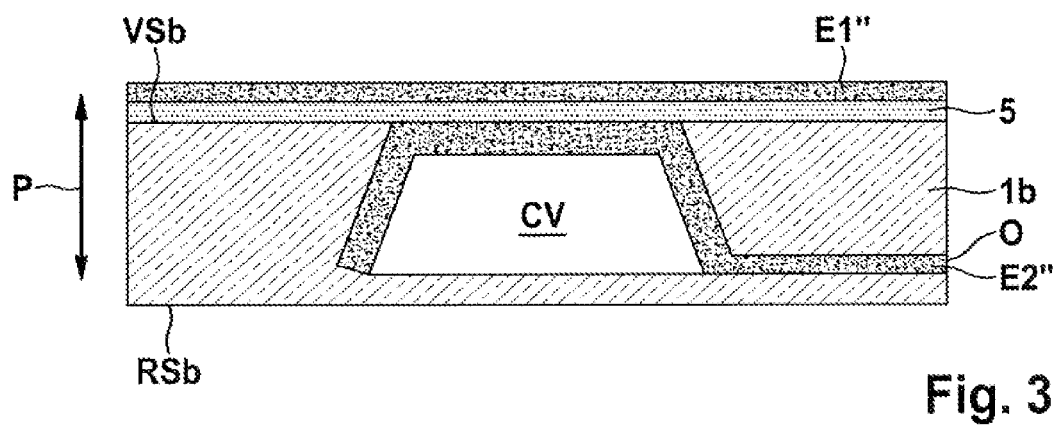
FIG. 3 shows a schematic cross-sectional view to explain a micromechanical solid-electrolyte sensor device according to a third embodiment of the present disclosure.

FIG. 3 is a schematic cross-sectional view to explain a micromechanical solid-electrolyte sensor device according to a third embodiment of the present disclosure.

In the third embodiment, reference 1b denotes a carrier substrate, which has a front side VSb and a back side RSb. The carrier substrate 1b comprises a closed cavern CV, over which the solid-electrolyte membrane 5 extends on the front side VSb. Inside the closed cavern CV and below the solid-electrolyte membrane 5, the backside electrode E2" is provided, which is led out from the closed cavern CV through a corresponding opening O.

The front-side electrode E1" is applied on the front side on to the solid-electrolyte membrane 5.

In another embodiment (not shown) only a locally porosified region, which is closed on the back side, may also be used as the cavity or cavern.

Figure 4A:
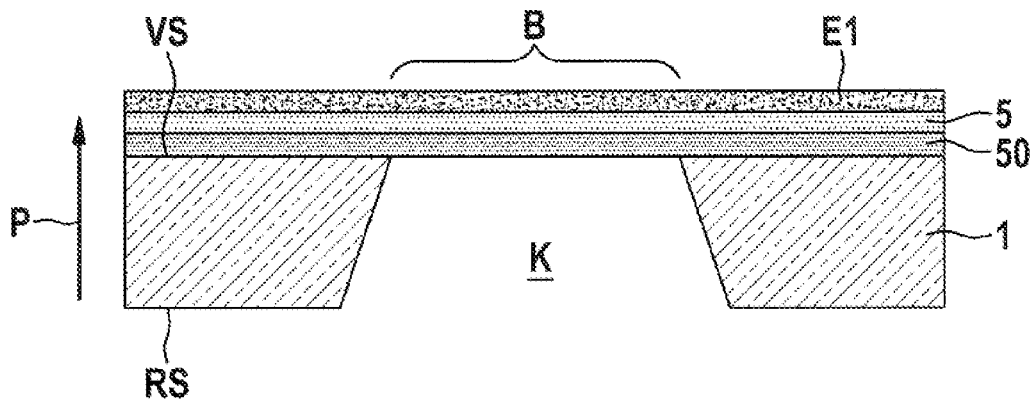
FIGS. 4a and 4b show schematic cross-sectional views to explain a production method of a micromechanical solid-electrolyte sensor device according to a fifth embodiment of the present disclosure.
Figure 4B:
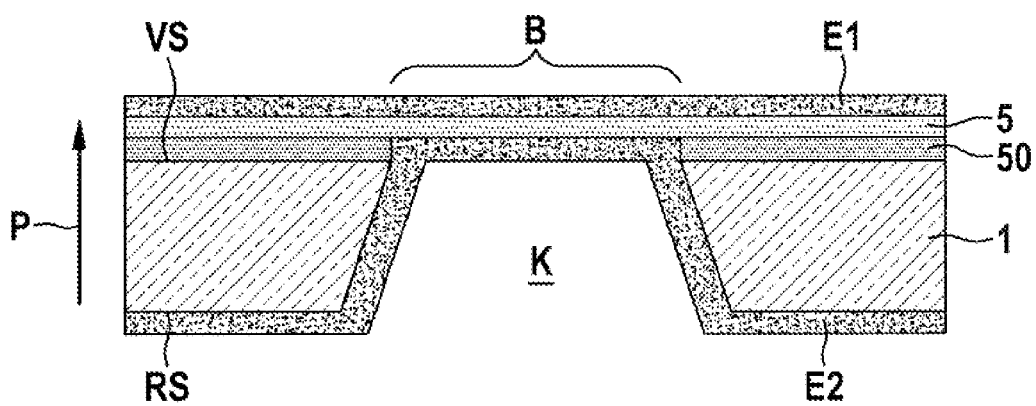

FIGS. 4a and 4b are schematic cross-sectional views to explain a production method of a micromechanical solid-electrolyte sensor device according to a fifth embodiment of the present disclosure.

In the fourth embodiment, an auxiliary membrane 50, for example consisting of silicon nitride or silicon oxide, is provided on the front side VS of the substrate 1 before the cavern K is etched.

The cavern K is subsequently etched, and then the solid electrolyte 5 and the first porous electrode E1 are provided on the front side VS, which leads to the process state according to FIG. 4a.

Subsequently, with reference to FIG. 4b, the auxiliary membrane 50 is removed from the back side RS in the membrane region B and the second porous electrode E2 is subsequently provided on the back side RS.

In this embodiment, the auxiliary membrane 50 remains outside the sensor region 50, but this does not have a perturbing effect on the sensor function.

Figure 5A:
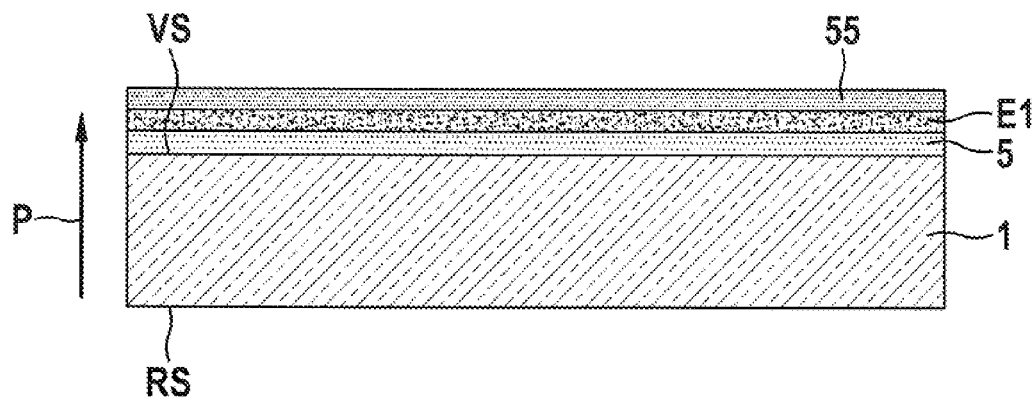
FIGS. 5a and 5b show schematic cross-sectional views to explain a production method of a micromechanical solid-electrolyte sensor device according to a sixth embodiment of the present disclosure.
Figure 5B:
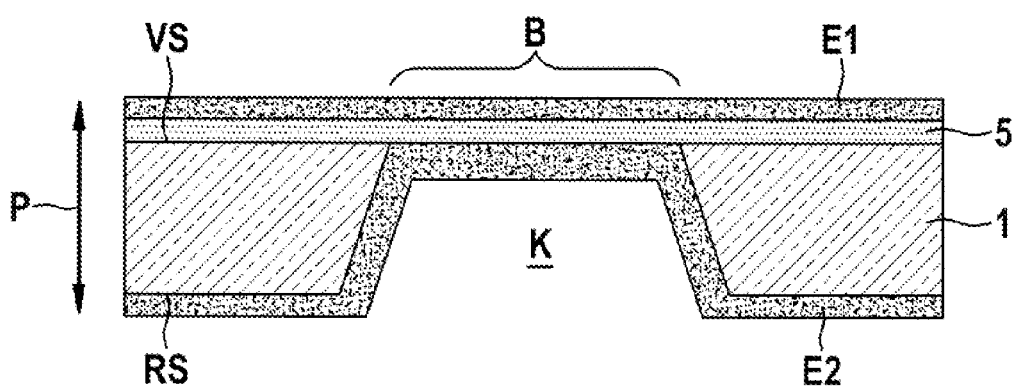

FIGS. 5a and 5b are schematic cross-sectional views to explain a production method of a micromechanical solid-electrolyte sensor device according to a sixth embodiment of the present disclosure.

In the fifth embodiment, the solid electrolyte 5 and the first porous electrode E1 are provided on the front side VS of the substrate 1 before the cavern K is etched. An auxiliary membrane 55, for example consisting of silicon nitride or silicon oxide or a polymer, is subsequently provided as etching protection on the front side VS of the substrate 1, i.e. on the first porous electrode E1, which leads to the process state according to FIG. 5a.

Subsequently, with reference to FIG. 5b, the cavern K is etched and then the second porous electrode E2 is provided on the back side RS. Finally, the auxiliary membrane 55 on the front side 55 is removed.

A material which is stable at high temperatures and chemically inert may preferably be used as the material for the carrier substrate 1 in the embodiments presented, for example a wafer of monocrystalline silicon carbide (SiC).

This offers the advantage that integrated semiconductor circuits which undertake signal preprocessing, for example in the form of amplifier circuits, regulating or control circuits, can be applied onto the wafers, in particular outside the regions for the Nernst cells or pump cells. These circuits are expediently already produced and processed before the pump cells are produced in the substrate. With these circuits, for example, oscillating operation of a pump cell can be carried out, the applied voltage and pumping direction being changed regularly. The signal evaluation may in this case be carried out on the basis of the time dependency and/or voltage dependency of the pump current.

Polycrystalline materials, for example polycrystalline SiC wafers, or multiphase materials, for example SiC in a silicon matrix, may also be used as the material for the carrier substrate, in which case circuits can only be produced in additional epitaxially grown layers. In the case of multiphase materials, porosification can be simplified, or carried out by extraction of a phase.

The gas-permeable electrodes E1, E2, or E1', E2', or E1", E2" may, for example, be produced by gas-flow sputtering of metals, and preferably noble metals, which permits high oxidation resistance at high working temperatures. By means of gas-flow sputtering, an electrically conductive but porous layer can be applied as the electrodes E1, E2. Other methods for the electrode production would, for example, be the application of noble metal nanoparticles in organic solution and a subsequent baking step for compaction of the particles.

The use of MEMS structures for combining a plurality of chemical sensors, or different functions for a sensor, for example in use as a nitrogen oxide gas sensor, is particularly advantageous. In one embodiment of this gas sensor, a miniaturized double-chamber sensor with a pump cell and Nernst cell is produced. By virtue of the miniaturization, the more advantageous ratios between volume and surface area for the pump cell can be utilized for the detection of e.g. NO. The use of SiC semiconductor material as base material permits the integration of electrical circuits within the sensor chip for operation of the sensor and for amplification and preprocessing of the signals. In this way, an additional electronic unit between the sensor element and motor control unit can be simplified or entirely obviated.

Besides chemical sensors, for example chemFETs produced in an SiC carrier substrate with a nanostructured coating, detectors for electrical, thermal or mechanical information may also be fitted on the semiconductor substrates, for example field-sensitive transducers, piezoresistive elements and thermistors. In this way, further physical sensors for pressure, temperature or flow may be fitted on a membrane and integrated with the chemical sensor elements in a single component, for example as exhaust gas sensors for a plurality of chemical and physical parameters. Likewise, the actuators, for example for miniaturized valves or as heating resistors, may be integrated in a carrier substrate produced or further processed by the micromechanical method.

Although the present disclosure has been described with the aid of preferred exemplary embodiments, it is not restricted thereto. In particular, the materials and topologies mentioned are merely exemplary and not restricted to the examples explained.

The invention claimed is:

1. A micromechanical solid-electrolyte sensor device comprising:

a micromechanical carrier substrate having a front side, a back side, and a porosified region;
a first porous electrode and a second porous electrode; and
a solid electrolyte embedded between the first porous electrode and the second porous electrode.

2. The micromechanical solid-electrolyte sensor device according to claim 1, wherein:
the first porous electrode, the second porous electrode, and the solid electrolyte, embedded between the first porous electrode and the second porous electrode are above the porosified region.

3. The micromechanical solid-electrolyte sensor device according to claim 1, wherein the micromechanical carrier substrate is part of a wafer.

4. The micromechanical solid-electrolyte sensor device according to claim 3, wherein the wafer includes one of Si, SiC, and sapphire.

5. A micromechanical solid-electrolyte sensor device comprising:
a micromechanical carrier substrate having a front side and a back side;
a first porous electrode and a second porous electrode; and
a solid electrolyte embedded between the first porous electrode and the second porous electrode wherein;
the carrier substrate includes a closed cavern, and
the second porous electrode extends into the closed cavern.

6. The micromechanical solid-electrolyte sensor device according to claim 5, wherein the micromechanical carrier substrate is part of a wafer.

7. The micromechanical solid-electrolyte sensor device according to claim 6, wherein the wafer includes one of Si, SiC, and sapphire.

8. A method for producing a micromechanical solid-electrolyte sensor device, comprising:
applying a first porous electrode and a second porous electrode and a solid electrolyte, embedded between the first porous electrode and the second porous electrode, onto a micromechanical carrier substrate having a front side, a back side and a cavern closed by at least one of the first and second porous electrode and solid electrolyte.

9. The method according to claim 8, wherein applying the second porous electrode includes applying the second porous electrode in such a way that the second porous electrode extends into the closed cavern of the carrier substrate.

10. The method according to claim 8, wherein applying the second porous electrode further includes:
etching the cavern in the carrier substrate, wherein the carrier substrate has an auxiliary membrane on a front side;
applying the solid electrolyte and the first porous electrode on the front side;
removing the auxiliary membrane from a back side of the carrier substrate; and
applying the second porous electrode in such a way that the second porous electrode extends into the cavern.

11. The method according to claim 8, wherein applying the second porous electrode further includes:
applying an auxiliary membrane on a front side of the carrier substrate, wherein the solid electrolyte and the first porous electrode are on the front side;
etching the cavern in the carrier substrate;
applying the second porous electrode in such a way that it extends into the cavern; and
removing the auxiliary membrane on the front side.

* * * * *